United States Patent [19]

Gandolfi et al.

[11] Patent Number: 5,336,676

[45] Date of Patent: Aug. 9, 1994

[54] [3H,7H]THIAZOLO[3,4-A]PYRIDINES WITH ANTIASTHMATIC AND ANTIINFLAMMATORY ACTIONS ON THE RESPIRATORY TRACT

[75] Inventors: Carmelo A. Gandolfi; Giampiero De Cillis; Giorgio Long; Licia Gallico, all of Milan, Italy

[73] Assignee: Boehringer Mannheim Italia S.p.A., Milan, Italy

[21] Appl. No.: 949,629

[22] PCT Filed: Jun. 4, 1991

[86] PCT No.: PCT/EP91/01028

§ 371 Date: Dec. 4, 1992

§ 102(e) Date: Dec. 4, 1992

[87] PCT Pub. No.: WO91/18906

PCT Pub. Date: Dec. 12, 1991

[30] Foreign Application Priority Data

Jun. 8, 1990 [IT] Italy ............... 20585 A90

[51] Int. Cl.⁵ ............... A61K 31/54; A61K 31/535; A61K 31/495; A61K 31/50
[52] U.S. Cl. ............... 514/222.5; 514/233.2; 514/228.2; 514/253; 514/301; 546/114; 540/544; 544/61; 544/145; 544/215; 544/333
[58] Field of Search ............... 514/222.5, 233.2, 228.2, 514/253, 301; 546/114; 540/544; 544/61, 145, 215, 333

[56] References Cited

U.S. PATENT DOCUMENTS 4,946,955 8/1990 Hosomi ............... 544/234

*Primary Examiner*—Mukund J. Shah
*Assistant Examiner*—Matthew V. Grumbling
*Attorney, Agent, or Firm*—Nikaido, Marmelstein, Murray & Oram

[57] ABSTRACT

Compounds of formula (I)

(I)

(a)

wherein R is an alkyl group; $R_1$ is a cyano, carboxy, alkoxycarbonyl or hydroxylaminocarbonyl group; $R_2$ is substituted or unsubstituted phenyl ($C_3$-$C_7$)-cycloalkyl, α-, β- or γ-pyridyl or a benzoheteroxcyclic ring; $R_3$ is carboxy or carboalkoxy; Y is a group of the formula —COOX; —NHCOA; —NCO; —COA; —CONHOR$_e$; —OCOA; A; —COCH$_2$COR$_f$; —NHCSA; —OCSA; (a); X is hydrogen, alkyl or succinimidyl group; A is a cyclic or acyclic amino group; and n is 1 or 2; having pharmacological characteristics which render them useful in the treatment of inflammatory conditions of the respiratory tract and asthmatic conditions.

7 Claims, No Drawings

[3H,7H]THIAZOLO[3,4-A]PYRIDINES WITH ANTIASTHMATIC AND ANTIINFLAMMATORY ACTIONS ON THE RESPIRATORY TRACT

The present invention relates to [3H, 7H]thiazolo[3,4-a]-pyridines, a method for preparing them and pharmaceutical compositions which contain them.

More precisely the invention relates to compounds of formula (I)

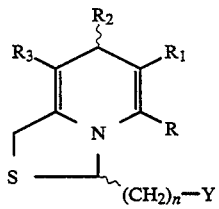

in which:

R is ($C_1$–$C_4$) alkyl;

$R_1$ is a cyano, free or salified carboxyl, alkoxycarbonyl, hydroxyaminocarbonyl group or a carboxyamide group of the formula

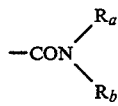

wherein Ra and Rb are as defined below or a group of the formula

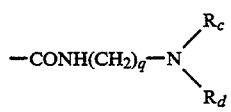

wherein q is an integer from 2 to 4; $R_c$ is hydrogen, $C_1$–$C_6$ alkyl, benzyl; Rd is hydrohydrogen or ($C_1$–$C_6$) alkyl or Rc and Rd, taken together with the nitrogen atom, form a pyrrolidine, piperidine, morpholine, thiomorpholine, ($C_1$–$C_4$) alkylpiperazine $R_2$ is a ($C_3$–$C_7$) cycloalkyl group, α, β or γ-pyridyl, substituted or unsubstituted phenyl or a bicyclic ring in which a benzene ring is fused to a 5- or 6-membered heterocyclic ring containing one or more heteroatoms selected from O, S and N, said bicyciic ring being preferably bound via the benzene ring;

$R_3$ is a free or salified carboxy group, an alkoxycarbonyl group or a —$CONR_aR_b$ or

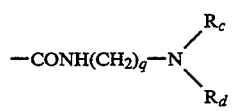

group defined above;

Y is one of the following groups: COOX; —NHCOA; —NCO; —COA; —$CONHOR_e$; —OCOA; A; —CO—$CH_2$—CO—$R_f$; —NHCSA;

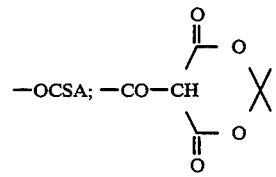

$R_e$ is hydrogen, ($C_1$–$C_6$) alkyl, or substituted or unsubstituted phenyl or benzyl; $R_f$ is ($C_1$–$C_6$) alkoxy,

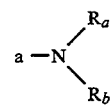

group wherein $R_a$ and $R_b$ are as defined below or a (pyridin-2-yl)amino group; X is hydrogen, ($C_1$–$C_4$) alkyl, allyl, propargyl or an N-succinimidyl group of formula

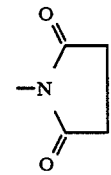

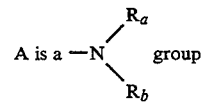

wherein $R_a$ or $R_b$, which are the same or different, are hydrogen, ($C_1$–$C_4$) alkyl, allyl, propargyl, ($C_3$–$C_7$) cycloalkyl, unsubstituted or substituted phenyl, benzyl unsubstituted or subs tituted by hydroxy and/or methoxy groups, benzhydryl unsubstituted or substituted by halogens or, taken together with the nitrogen atom, they form an aziridine, azetidine group or a ring of formula

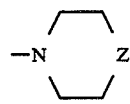

wherein Z is O, S, $CH_2$ or -S-S- or a ring of formula

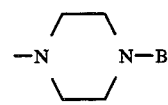

wherein B is hydrogen, ($C_1$–$C_4$) alkyl, benzyl unsubstituted or substituted by hydroxy and/or alkoxy groups, benzhydryl unsubstituted or substituted by halogen atoms, unsubstituted or substituted phenyl, 5- to 6-membered heterocycle with 1-3 nitrogen atoms unsubstituted or substituted by 1 or 2 amine, monoalkyl-, monoalkenyl- or monoalkynyl-amine, dialkylamine, alkylalkenylamine, piperidin-1-yl, morpholin-4-yl, pyrrolidin-1-yl groups; n is the integer 1 or 2.

The expression "unsubstituted or substituted phenyl" as used above refers to a phenyl ring containing from 1 to 3 substituents selected from the group of ($C_1$–$C_4$) alkyl such as methyl, ethyl, propyl, isopropyl, tert-butyl; ($C_1$–$C_4$) alkoxy such as methoxy, ethoxy or propoxy; ($C_1$–$C_4$) alkylthio such as methylthio, ethylthio; phenoxy; 4-hydroxyphenoxy; phenylthio; 4-hydroxyphenylthio; halogen atoms (chlorine, bromine, fluorine); the following groups: cyano, azide, nitre, amine, ($C_1$–$C_6$) acylamino, trihaloacetylamino such as trifluoroacetylaminc, methane- or trifluoromethanesulphonamido, benzene- or para-tolyl-sulphonamido, trihalomethyl, dihalomethoxy such as difluoromethoxy, trifluoromethoxy groups, a free or salified carboxy group and ($C_1$–$C_4$) alkoxycarbonyl.

Particularly preferred examples of mono- and/or polysubstituted phenyl groups are those bearing the following substitutions: 2-chloro-, 3-chloro-, 4-chloro-, 2,3-dichloro-, 2-fluere-, 2-fluoro-3-chloro-, 2-nitre-, 6-fluere-2,3-dichloro-, 3-nitre-, 3-nitro-4-phenoxy-, 4-nitr0-, 4-nitro-3-phenoxy-, 2-trifluoromethyl-, 3-trifluoromethyl-, 3-cyano-, 3-methoxy-, 2amino-, 3-amino-, 4-amine-, 2-methanesulphonamido-, 3-methanesulphonamido-, 4-methanesulphonamido-, 3-methanesulphonamido-4-phenoxy-, 4-methanesulphonamido-3phenoxy-, 4-fluoro-2,3-dichloro-, 3-carboxy-4-hydroxy-, 3-hydroxy-4-carboxy- and combinations thereof.

When $R_2$, $R_a$ or $R_b$ are a ($C_3$–$C_7$) cycloalkyl group, this is preferably cyclopropyl, cyclopentyl or cyclohexyl. When $R_1$ or $R_3$ are a carboxyester group this is preferably a ($C_1$–$C_4$) alkyl, allyl, propargyl, benzyl, p-methoxybenzyl, benzhydryl, trityl or trichloroethyl ester.

When $R_2$ is a bicyclic ring wherein a benzene ring is fused to a 5- to 6-membered heterocyclic ring, said bicyclic ring preferably benzo-1,3-dioxolan-4-yl, 1,4-benzodioxolan-6-yl, 1,4-benzodioxolan-5-yl, benzofuran-4-yl or benzofurazan-4-yl.

$R_2$ is preferably 3-chlorophenyl, 3-nitrophenyl, phenyl, cyclohexyl, 2,3-dichlorophenyl.

When B is a 5- to 6-membered heterocyclic ring containing from 1 to 3 nitrogen atoms, this is preferably pyridin-2-yl, pyrimidin-4-yl, pyrimidin-2-yl or 1,3,5-triazinyl-2-yl, optionally substituted by 1 or 2 amino groups such as amino, monoalkylamino (methylamino, ethylamino), 2-propenylamino, 2-propynylamino, propylamino, isopropylamino or dialkylamino such as dimethylamino, diethylamino, ethylallylamino and the like.

Particularly preferred meanings when B is a heterocyclic group are the following ones: 2-amino-5-(1-pyrrolidinyl)-phenyl, 2-pyridyl-methyl, 2-pyridyl, (3-hydroxy-2-pyridynyl)-methyl, [2,6-bis(diethylamino)-4-pyrimidinyl], [2,6-bis(allylamino)-4-pyrimidinyl], [2,6-bis(1-pyrrolidinyl)-4-pyrimidinyl], [2,6 bis (diethylamino) -3-benzoyl-4-pyrimidinyl], [2,6-bis-(diethylamino)-3-acetyl-4-pyrimidinyl], [2,6-bis (1-pyrrolidinyl)-3-acetyl-4-pyrimidinyl], [2,6-bis(1-pyrrolidinyl-3-benzoyl-4 -pyrimidinyl], [4,6-bis (2-propenylamino)-1,3,5-triazin -2-yl], [4,6-bis (2-diethylamino)-1,3,5-triazin2-yl], [4,6-bis(1-pyrrolidinyl)-1,3,5-triazin2-yl], [3,6-bis(diethylamino)-pyridin-2-yl], [3,6-bis(diethylamino)-pyridin-2-yl], [3,6-bis(1-pyrrolidinyl)-pyridin-2-yl], [3,6-bis (allylamino) -pyridin-2-yl], [3,6-bis (propargylamino) -pyridin-2-yl], [3,6-bis (N-e-thyl, N-allylamino)-pyridin-2-yl].

Compounds (I) which are particularly preferred are those in which $R_1$ and $R_3$ groups are alkoxycarbonyl groups, in particular methoxycarbonyl, ethoxycarbonyl, iscoropoxycarbonyl, allyloxycarbonyl and tert-butoxycarbonyl or those in which one of $R_1$ or $R_3$ is a cyano or carboxyamido group as defined above; $R_2$ is an unsubstituted or substituted phenyl group as defined above R is methyl; n is 1 or 2 and Y is a —COA, —OCOA or A group.

Even more particularly preferred compounds are those in which:

Y is A and n is 2;

Y is —COA, n=1 and $R_2$ is phenyl or cycloalkyl as defined above;

Y is —NHCOA and n=1 or 2;

Y is

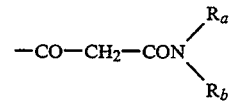

and n=1;

Y is —CONHOH or —OCOA and n=1 or 2.

When the compounds of formula (I) contain an acid or basic group, this can be salified respectively with pharmaceutically acceptable bases or acids. The non-toxic salts thus obtained are included in the invention as well as the single enantiomers, racemates and diastereoisomers or mixtures thereof of the compounds of formula (I). In particular, said compounds of formula I contain 2 chiral carbon atoms in positions 3 and 7 and thus syn and anti geometries can be defined, corresponding to the formulae (Ia) and (Ib) indicated below:

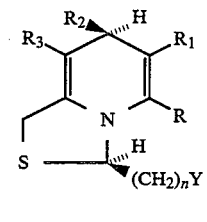 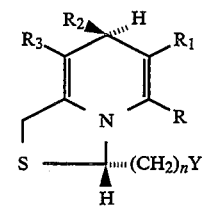

Ia syn          Ib anti

The compounds of formula (I) will be indicated below as syn-[3H, 7H]thiazolo[3, 4-a]pyridines or simply as [3H,7H]thiazolo[3,4-a]pyridines. The compounds of formula (Ib) on the other hand will be indicated as anti-[3H,7H]thiazolo[3,4-a]pyridines whereas the diastereoisomeric mixtures will be indicated as (s,a) -[3H, 7H]thiazolo[3,4-a]pyridines.

Both the compounds of formula (I a) and those of formula (Ib), obtained from racemic dihydropyridines, are racemic mixtures. Wherever optically active products are mentioned, the compounds (Ia) will be indicated as (+)- cr (-)-Syn-[3H,7H]thiazolo[3,4-a]pyridines or simply (+)- or (-)-[3H,7H]thiazolo[3,4-a]pyridines; the ccmpounds (Ib) will on the other hand be indicated as (+)- or (-)-anti[3H,7H]thiazolo[3,4-a]pyridines.

The compounds of the invention of formula (I) are prepared by a process which consists in reacting a Michael acceptor of formula (IIa) or (IIb):

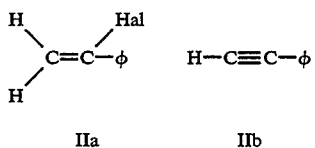

IIa  IIb wherein Hal is a halogen atom (chlorine, bromine or iodine) and the symbol φ is a carboxyester, chlorocarbonyl, cyano, azidocarbonyl,

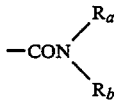

($C_1$-$C_4$) alkylcarbonyl, benzoyl or ($C_7$-$C_{10}$) alkylarylcarbonyl electrophilic group, with a 1,4-dihydropyridine of formula (III)

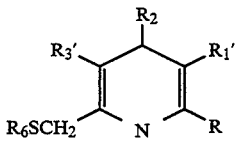

wherein R and $R_2$ are as defined above; $R_1'$ and $R_3'$ have the same meanings as $R_1$ and $R_3$ excluding the free or salified carboxyl group;

$R_6$ is hydrogen, ($C_2$-$C_6$) acyl, benzoyl or a group of formula C(=NH)—$NH_2$ or C(=NH)—$NH_2 \cdot H^+P^-$ wherein $P^-$ is the counterion of an inorganic or organic acid such as, for example, hydrochloric, hydrobromic, acetic, camphorsulphonic, mandelic, tartaric or 0,0-dibenzoyltartaric acids.

The reaction between compound II and compound III, usually carried out in an inert solvent and in the presence of a suitable base, leads to compounds of formula (Ic)

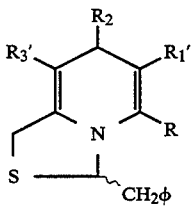

wherein R, $R_1'$, $R_2$, $R_3'$ and the symbol φ are as defined above, in the form of a syn, anti diastereoisomeric mixture, with a prevalence of the syn diastereoisomer. The compounds of formula (Ic) thus obtained can therefore be subjected to separation into the single diastereoisomers or can be converted into other compounds of formula (I), by means of conventional reactions such as, for example:

a) saponification of a carboxyester group into the corresponding carboxy group which in turn can be transformed into succinimide ester, acyl chloride, mixed anhydride or other known activated derivatives of the carboxy group;

b) reaction of the acids or the activated derivatives of the acids obtained according to a) with amines of formula $NHR_aR_b$, hydroxyl amine or azides of an alkali metal; in the latter case azides of carboxylic acids are obtained which, when subjected to Curtius rearrangement, provide C—nor isocyanates which can in turn be converted into C—nor amines or C—nor ureides;

c) reduction of the free carboxylic group or its corresoonding mixed anhydride or a carboxyester group to primary alcohol ($CH_2OH$) which, after transformation into the corresponding halide or sulphonate, can be converted into alkylamine by reaction with an amine of formula $NHR_aR_b$; suitable reducing agents include diborane or a borohydride of an alkaline or alkali earth metal;

d) the alcohols obtained according to d) can be converted into the corresponding azides by Mitsunobu reaction with hydrazoic acid or, after transformation into the corresponding halide or sulphonate, by reaction with the azide of an alkali metal. The above-mentioned alkylazides can be converted into amines by reduction, for example with trialkyl- or triarylphosphines trialkyl phosphites, hydrides of alkali metals, alkaline earth metals etc;

e) the alcohols obtained according to d) and the amines obtained according to e) can be converted respectively into carbamates or thiocarbamates and ureas or thioureas by reaction with carbonyldiimidazole or thiocarbonyl-diimidazole and subsequently with an amine of formula $NHR_aR_b$;

f) reduction of the aromatic nitro groups possibly present in the compounds of formula (Ic);

g) acyl ation of the primary and secondary amino groups present in the compounds of formula (Ic), to give the corresponding amides and sulphonamides by reaction with halides or anhydrides of carboxylic, alkylsulphonic or arylsulphonic acids;

h) transformation of the keto groups present in the compounds (Ic) into the corresponding oximes and subsequent Beckmann rearrangement to the corresponding amides of formula (I);

i) salification and/or separation of optical, geometric or diastereoisomeric isomers according to conventional methods;

l) the acids or activated derivatives of the acids obtained according to a) can be reacted with a Meldrum acid and subsequently with an alcohol or an amine of formula $NHR_aR_b$, obtaining respectively a β-ketoester or a β-ketoamide.

The reaction between compounds (II) and (III) brings about the formation of intermediates of formula (IVa) or (IVb)

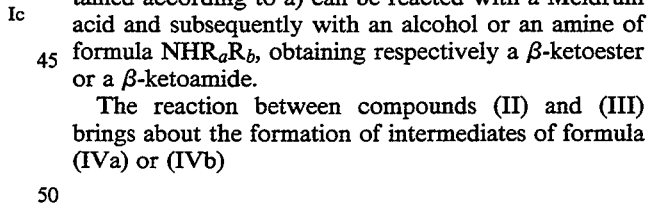

which can then be cyclized to compounds of formula (Ic) without the need to isolate the intermediate.

The Michael accepters of formula II are known and can therefore be prepared by conventional methods;

some of them are also available commercially. In particular the following compounds are of particular relevance within the scope of this invention among those generically embraced by formula II: a) esters or amides of propargyl acid or propargylketones; b) α-halo-acryl esters or amides (for example, α-halo-acryloyl chloride, obtainable from acrylic esters or amides by addition of halogen and subsequent dehydrohalogenation); c) α-halo-α,β-vinylketones, which can be prepared by conventional methods from α,β-vinylketones by addition of halogen and subsequent dehydrohalogenation.

The 1,4-dihydropyridines of formula (III) are known from W087/00836 (12.02.1987) or can be prepared according to the methods described in said international application. Said compounds of formula (III) can be utilised both as racemates or as pure enantiomers useful method for the preparation of pure enantiomers of compounds of formula (III) is described in Italian Patent Application no. 19477A/89 which provides teachings for the optical resolution of isothiouronium salts with optically active acids.

Piperazines of formula

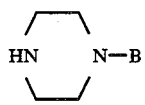

are described in W087701706 (26.03.1987).

The compounds of the invention are effective in the prevention and/or reduction of hyper-reactivity of the respiratory tract and in the treatment of the phlogistic condition which accompanies the acute and sub-chronic inflammation of bronchial mucosa.

Brenchial hyper-reactivity is a clinical symptom of asthma and it is caused by abnormal and latent contractility sensitivity of the bronchial mucosa.

Bronchial hyper-reactivity can cause acute crisis of asthma after physical practice, and or after exposure to external stimuli such as the inhalation of fog, pollutants, allergens and auracolds.

Much of the typical phenomenology of the bronchial hyper-reactivity states can be simulated by an experimental model which consists in the forced inhalation cf tobacco smoke (for 10 minutes, for example) by male guinea pigs with a body weight of 400 to 450 g, in artificial respiration under anaesthesia by ethylurethane and pancuronium bromide.

The action of the compounds of the invention, in the pharmacological model considered, is demonstrated by the normalization of parameters which become changed after the forced inhalation of tobacco smoke, such as: persistent increase in the pulmonary inspiratory pressure (measured according to the technique of Konzett and Rossler, Naun. Schmied. Arch. Exper. Pathol. Pharmacol. 191, 71, 1970); increased cell count (leucocytes, eosinophiles, epithelial cells) in the bronchoalveolar lavage liquids (BAL); transudation into the bronchial tissue (trachea) of Evans Blue dye previously administered intravenously.

The compounds of the invention, which are administered two hours before exposure to the tobacco smoke in dosages which vary between 2 and 50 mg/Kg, demonstrate a protective action which lasts at least 4–6 hours and results in a reduction of the increased pressure induced by the inspiration of smoke, accompanied by simultaneous normalization of the cell count in the EAL and by inhibition of the transudation of dye. Such pharmacological effects are related to the doses administered.

From what has been shown above it is clear that the compounds of the invention can be used in human therapy in the treatment of asthmatic and obstructive conditions of the respiratory tract, in the treatment of inflammatory phlogosis. In the therapeutic uses intended, the compounds of the invention will be administered in the form of pharmaceutical compositions which can be prepared with eccipients and conventional techniques such as, for example, those described in Remington's Pharmaceutical Sciences Handbook, Mack Pub. Co., N.Y., USA, 17th ed., 1985, adapted for administration by intramuscular, intravenous, oral, aerosol and rectal methods.

The daily dose will depend on several factors such as the gravity of the pathology and the condition of the patient: it will normally consist of from 1 to 50 mg of a compound of formula I for a patient weighing 70 kg, one or more times a day.

EXAMPLE 1

A solution of propargyl acid (84 μl) in dichloromethane (2 ml) is added with stirring and cooling (about −20° C.) to a solution of dicyclohexylcarbodiimide (DCC 0.28 g) in dichloromethane (2 ml); after about 20 minutes a solution of N-(3,6-bis-diethylaminopyridin-2-yl)piperazine (0.28 g) in dichloromethane (2 ml ) is added to the mixture over about 10 minutes. The temperature of the reaction mixture is allowed to return spontaneously to room temperature, the precipitate of dicycloesylurea is filtered and the filtrate is evaporated to dryness. The residue (0.6 g) is purified by column chromatography ($SiO_2$ g 18; eluant: hexane/ethylacetate 8:2) leading to 0.24 g of N-(3,6-bis-diethylaminopyridin-2-yl ) -N'-propargyloylpiperazine.

An aqueous solution of NaOH (35%, 0.14 ml) is added with stirring and under a nitrogen atmosphere to a suspension of S-[(6-methyl-5-methoxycarbonyl-3-ethoxycarbonyl-4-(3-nitrophenyl)-1,4-dihydropyridin-2-yl)methyl]-isothiouronium chloride (0.2.g), triethylbenzylammonium chloride (30 rag) and N-(3,6-bisdiethylamino-pyridin-2yl ) -N'-propargyloyl-piperazine (0.16 g) in benzene (2 ml) and stirring is continued at room temperature for 1 and a half hours. The solvent is evaporated to a small volume under vacuum, diluted with water and extracted repeatedly with AcOEt (2×3 ml ) . The organic extracts are dried over sodium sulphate and the solvent is evaporated under reduced pressure. The residue is purified by column chromatography ($SiO_2$ g 9; eluent: hexane/ethylacetate 7:3), to give 0.24 g of N-3,6-bis-diethylaminopyridin-2-yl)-N'-(2 -((5-methyl-6-methoxycarbonyl-7-(3-nitrophenyl) -8-ethoxycarbonyl )[-3H,7H]thiazolo[3,4-a]pyridin-3-yl)acetyl)-piperazine (m.p. 130° C. as hydrochloride).

EXAMPLE 2

By reacting a suspension of S-[(6-methyl-5-methoxycarbonyl -3-ethoxycarbonyl-4-(3-nitrophenyl) -1,4-dihydropyridin -2-yl)methyl]-isothiouronium chloride in benzene and triethylbenzylammonium chloride with the appropriate N-substituted N'-propargyloyl-piperazine (prepared from propargyl acid and N-substituted piperazines according to the process described on Example 1) in the presence of an aqueous solution of NaOH, the following (([3H,7H]thiazolo[3,4-a]pyridinyl)acetyl)piperazines were obtained:

N-methyl-N'-(2-(3-(5-methy 1-6-methoxycarbonyl-7-(3-nitrophenyl)-8-ethoxycarbonyl) (m.p. 128° C.);

N-benzyl-N'-(2-(3-(5-methyl-6-methoxycarbonyl-7-(3-nitrophenyl) -8-ethoxycarbonyl);

N-(3,4,5-trimethoxybenzyl)-N'-(2-(3-(5-methyl-6-methoxycarbonyl -7-(3-nitrophenyl)-8-ethoxycarbonyl);

N-(phenyl)-N'-(2-(3-(5-methyl-6-methoxyc arbonyl-7-(3-nitrophenyl)-8-ethoxycarbonyl);

N-(4-fluorophenyl)-N'-(2-(3-(5-methyl-6-methoxycarbonyl -7-(3-nitrophenyl)-8-ethoxycarbonyl);(m.p. 249°-2520°C.)

N-(benzhydryl)-N'-(2-(3-(5-methyl-6-methoxycarbonyl-7-(3-nitrophenyl) -8-ethoxycarbonyl);

N-(4, 4'-difluorobenzhydryl )-N'-(2-(3-(5-methyl-6-methoxycarbonyl -7-(3-nitrophenyl)-8-ethoxycarbonyl); (m.p. 234°-236° C.)

N-(2-pyridinyl-methyl )-N'-(2-(3-(5-methyl-6-methoxycarbonyl -7-(3-ni trophenyl)-8-ethoxycarbonyl);

N-(pyridin-2-yl)-N'-(2-(3-(5-methyl-6-methoxycarbonyl-7-(3-nitrophenyl)-8-ethoxycarbonyl);

N-(3-hydroxy-2-pyridinylmethyl )-N'-(2-(3-(5-methyl-6methoxycarbonyl-7-(3-nitrophenyl)-8-ethoxycarbonyl);

N-(2,6-bis-diethylamino-pyrimidin-4-yl )-N'-(2-(3-(5'methyl -6-metkoxycarbonyl-7-(3-nitrophenyl)-8-ethoxycarbonyl);

N-(2,6-bis-dial lyl aminopyridin-2-yl )-N'-(2-(3-(5-methyl -6-methoxycarbonyl-7-(3-nitrophenyl)-8-ethoxycarbonyl);

N-(2,6-bis(pyrrolidin-1-yl)pyrimidin-4-yl)-N'-(2-(3-(5-methyl -6-methoxycarbonyl-7-(3-nitrophenyl)-8-ethoxycarbonyl); (m.p. 195°-197° C.)

N-(4,6-bis-diethylamino-1,3,5-triazin-2-yl)-N'-(2-(3-(5-methyl-6-methoxycarbonyl-7-(3-nitrophenyl)-8-ethoxycarbonyl);

N-(4,6-bis(pyrrolidin-1-yl)-1,3,5-triazin-2-yl)-N'-(2-(3-(5-methyl-6-methoxycarbonyl-7-(3-nitrophenyl)-8-ethoxycarbonyl);

N-(3,6-bis(pyrrolidin-1-yl)-pyridin-2-yl )-N'-(2-(3-(5methyl -6-methoxycarbonyl-7-(3-nitrophenyl)-8-ethoxycarbonyl);

N-(3,6-bis-dime thyl amino-pyridin-2-yl )-N'-(2-(3-(5-methyl -6-methoxycarbonyl-7-(3-nitrophenyl)-8-ethoxycarbonyl);

N-(3,6-bis-allylamino-pyridin-2-yl )-N'-(2-(3-(5-methyl-6-methoxycarbonyl-7-(3-ni trophenyl)-8-ethoxycarbonyl);

N-(3,6-bis(N-ethyl,N-allylamino)-pyridin-2-yl)-N'-(2-(3-(5-methyl-6-methoxycarbonyl-7-(3-nitrophenyl)-8ethoxycarbonyl);

N-(3,6-bis-propargyl amino-pyridin-2-yl )-N'-(2-(3-(5-methyl-6-methoxycarbonyl -7-(3-nitrophenyl)-8-ethoxycarbonyl);

EXAMPLE 3

0.45 ml of methyl propargylate are added under an inert gas atmosphere at room temperature and with stirring, to a suspension of S-[(6-methyl-5-cyano-3-ethoxycarbonyl -4-(3-nitrophenyl)-1,4-dihydropyridin-2yl)methyl]-isothiouronium chloride(2 g) in MeOH/DMF (1/1, 40 ml); 35% aqueous NaOH (0.78 ml) is then added and stirring is continued for 24 hrs. Then further aqueous NaOH (0.39 ml of 35%) is added. Initially a complete solution of the reagents is observed, followed by the development of an intense red colouring which vanishes in time with contemporaneous precipitation of a solid which, over the next 12 hrs, dissolves again. The mixture is concentrated under vacuum, diluted with N HCl and extracted repeatedly with AcOEt. The unified organic extracts are washed with water, dried over $Na_2SO_4$ and evaporated to dryness. By crystallization of the residue from ethyl ether($Et_2O$), 1.69 g of 2-(3-(5-methyl-6-cyano- 7-(3-nitrophenyl)-8-ethoxycarbonyl) -[3H, 7H]thiazolo[3,4-a]pyridinyl)-acetic acid are obtained(m.p. 209°-210° C.).

A solution in tetrahydrofuran (THF; 15 ml) of hydroxysuccinimide (0.86 g ) and 1.5 g of the acid de scribed above is cooled to 0 ° C. and with stirring 4morpholinoethylisonitrile (0.63 ml ) is added. The mixture is keot for 30 minutes at room temperature and, after pouring into an excess of N HCl, is extracted with AcOEt; the organic extracts, after the usual workup, are evaporated to dryness to provide 3.5 mM of a crude N-hydroxysuccinimide ester of the 2-(3-(5'methyl6-cyano-7-(3-nitrophenyl)-8-ethoxycarbonyl -[3H, 7H]thiazolo[3,4-a]pyridinyl)-acetic acid which is dissolved in DMF (15 ml). 0.97 g of N-(2,6-bis(pyrrolidin-1-yl)-pyrimidin-4-yl )-piperazine are added to this solution. The mixture is kept at room temperature for 1 hour, diluted with water and extracted with AcOEt. After the usual work-up and crystallization of the residue from hexane/AcOEt, 1.8 g of N-(2,6-bis(pyrrolidin-1-yl) -pyrimidin-4-yl )-N'-2-(3-(5-methyl-6-cyano-7-(3-nitrophenyl)-8-ethoxycarbonyl-[3H,7H]thiazolo [3, 4-a]pyridinyl)acetyl)-piperazine, (m.p. 130°-132° C.) are obtained.

EXAMPLE 4

By reacting a solution in DMF of the N-hydroxysuccinimido ester of the 2-(3-(5-methyl-6-cyano-7-(3-nitrophenyl)-8-ethoxycarbonyl-[3H,7H]thiazolo[3, 4-a]pyridinyl)acetic acid with an amine selected from the group comprising: piperidine, morpholine, thiamorpholine, 4,5-dithiazepine, azetidine, aziridine, diethylamine, cyclopentylamine, cyclopropylamine, N-(3,5-dimethoxy-4-hydroxybenzyl)-piperazine, N-(2-amino-5-(pyrrolidin-1-yl-phenyl) piperazine, O-benzyl-hydroxylamine, the following compounds are prepared:

N-(2-(3-(5-methyl-6-cyano-7-(3-nitrophenyl)-8-ethoxycarbonyl) -[3H,7H]thiazolo[3,4-a]pyridinyl)-acetyl)-piperidine;

N-(2-(3-(5-methyl-6-cyano-7-(3-nitrophenyl)-8-ethoxycarbonyl) -[3H,7H]thiazolo[3,4-a]pyridinyl)-acetyl)-morpholine;

N-(2-(3-(5-methyl-6-cyano-7-(3-nitrophenyl)-8-ethoxycarbonyl) -[3H,7H]thiazolo[3,4-a]pyridinyl)-acetyl)-thiamorpholine;

N-(2-(3-(5-methy 1-6-cyano-7-(3-nitrophenyl)-8-ethoxycarbonyl) -[3H,7H]thiazolo[3,4-a]pyridinyl)-acetyl)-4,5dithiazepine;

N-(2-(3-(5-methyl-6-cyano-7-(3-nitrophenyl)-8-ethoxycarbonyl) -[3H,7H]thiazolo[3,4-a]pyridinyl)-acetyl)-azetidine;

N-(2-(3-(5-methyl-6-cyano-7-(3-nitrophenyl)-8-ethoxycarbonyl) -[3H,7H]thiazolo[3,4-a]pyridinyl)-acetyl)-azitidine;

N,N-diethyl, 2-(3-(5-methyl-6-cyano-7-(3-nitrophenyl)-8-ethoxycarbonyl) -[3H,7H]thiazolo[3,4-a]pyridinyl)-acetamide;

N-(3,5-dimethoxy-4-hydroxy-benzyl )-N'-(2-(3-(5-methyl6-cyano-7-(3-nitrophenyl)-8-ethoxycarbonyl)-[3H,7H]-thiazolo[3,4-a]pyridinyl)-acetyl)-piperazine;

N-(2-amino-5-(pyrrolidin-1-yl)-phenyl)-N'-(2-(3-(5-methyl-6-cyano-7-(3-nitrophenyl)-8-ethoxycarbonyl)-[3H,7H]thiazolo[3,4-a]pyridinyl)-acetyl)-piperazine;

N-benzyloxy, 2-(3-(5-methyl-6-cyano-7-(3-nitrophenyl)-8-ethoxycarbonyl) -[3H,7H]thia zolo[3,4-a]pyridinyl)-acetamide;

N-cyclopentyl,2-(3-(5-methyl-6-cyano-7-(3-nitrophenyl)-8-ethoxycarbonyl)-[3H,7H]thiazolo[3,4-a]pyridinyl)-acetamide;

N-cyclopropyl,2-(3-(5-methyl-6-cyano-7-(3-nitrophenyl)-8-ethoxycarbonyl)-[3H,7H]thiazolo[3,4-a]pyridinyl)-acetamide;

EXAMPLE 5

Methyl propargylate(4.2 ml ) and aqueous NaOH (35%, 10.8 ml) are added in succession under an inert gas atmosphere at room temperature and with stirring, to a suspension of S-[(6-methyl-5-methoxycarbonyl -3-ethoxycarbonyl-4-(3-nitrophenyl)-1,4-dihydropyridin-2-yl)methyl]-isothiouronium chloride(20 g) in MeOH(200 ml). After the reagent s have completely dissolved the separation of a precipitate begins. This precipitate is re-dissolved by the addition of DMF (75 ml). Stirring is continued for a further 24 hrs; a second precipitate then separates which is filtered to obtain 9.7 g of methyl 2-(3-(5-methyl-6-methoxycarbonyl-7-(3-nitrophenyl) -8-ethoxycarbonyl) [3H,7H]thiazolo[3,4-a]pyridinyl)acetate (m.p. 158°-160° C.). The mother liquors are concentrated to a small volume, diluted with water and acidified with dilute HCl to pH 1. After extraction with AcOEt and subsequent usual work-up, a residue (8 q) is obtained by evaporation of the solvent. The residue is purified on silica gel column (250 g, eluant hexane/AcOEt/AcOH 80/15/5) to give 6.7 g of 2-(3-(5-methyl -6-methoxycarbonyl-7-(3-nitrophenyl) -8-ethoxycarbonyl)[3H,7H]thiazolo[3,4-a]pyridinyl) acetic acid (sodium salt, m.p. 270°-272° C. with decomposition).

4-morpholinoethyl isonitrile(2.4 ml ) is added dropwise to a solution, cooled to about 0 ° C., of 3.4 g of N-hydroxysuccinimide and 6.5 g of said acid in THF (50 ml). The resulting solution is kept at room temperature for 2 hrs, and concentrated under vacuum to 1/5 of the volume. After dilution with N HCl, the solution is extracted exhaustively with AcOEt. The organic extracts are washed with water, dried over sodium sulphate and evaporated to dryness under vacuum to give 7.2 g of N-hydroxysuccinimido ester of the 2-(3-(5-methyl-6-methoxycarbonyl-7-(3-nitrophenyl)-8-ethoxycarbonyl) [3H,7H]thiazolo[3,4-a]pyridinyl) acetic acid (m.p. 228°-229° C.).

EXAMPLE 6

5 ml of an aqueous solution of soditun azide is added to a solution of 2.3 g of N-hydroxysuccinimido ester of 2-(3-(5-methYl-6-methoxycarbonyl-7-(3-nitrophenyl) -8-ethoxycarbonyl) [3H,7H]thiazolo[3,4-a]pyridinyl)acetic acid in acetone (20 ml), cooled to −20° C. After 24 hrs the mixture is poured into water and ice and then extracted with benzene (3×10 ml). The unified organic extracts are washed with water (3×5 ml), dried over sodium sulphate and filtered to give a solution in benzene of 2-(3-(5-methyl-6-methoxycarbonyl-7-(3-nitrophenyl) -8-ethoxycarbonyl) [3H,7H]thiazolo[3,4-a]pyridinyl) acetylazide; this solution is immediately heated at gentle reflux until no more nitrogen is produced (about 3 hrs). After the solvent is evaporated, 1.7 g of 2-(3-(5-methyl -6-methoxycarbonyl-7-(3-nitrophenyl)-8-ethoxycarbonyl) [3H,7H]thiazolo[3,4-a]pyridinyl)methylisocyamate are obtained.

The solution of the above isocyanate (1.6 g) and N-(3,6-bis-diethylaminopyridin-2-yl)piperazine (1.1 g) in anhydrous acetonitrile (20 ml ) is heated under reflux for 2 hrs and evaporated to dryness. The residue is purified on silica gel column (70 g, eluant hexane/AcOEt 70/30) to give 1.94 g of N-(3,6-bis-diethylaminopyridin-2-yl ) -N'-(2-(3-(5-methyl-6-methoxycarbonyl -7-(3-nitrophenyl)-8-ethoxycarbonyl)-[3H,7H]thiazolo [3,4- a]pyridinyl) methylaminocarbonyl)-piperazine.

$^1$H NMR (200 MHz) $\delta$0.95 (t, J=7.1Hz, 6 H), 1.05 (t, J=7.1Hz, J=6 IS), 1.28 (t, J=6.5Hz, 3H), 2.65 (s, 3H), 2.96 (q, J=7.1, 4H), 3.4 (m, 10H), 3.5 (q, J=7.1, 4 H), 3.67 (s, 3 H), 4.15 (m, 2 H), 4.17 (d, J=18 Hz, 1 H), 4.66 (d, J=18 Hz, 1 H), 5.18 (s, 1H), 5.26 (t, J=5 Hz, 1 H), 5.73 (t, J=7.5 Hz, 1H), 6.03 (d, J=8 Hz, 1H), 7.10 (d, J=8 Hz, 1 H), 7.45 (dd, J=7.8 Hz, 1H), 7.67 (d, J=8 Hz, 1H), 8.05 (d, J=7 Hz, 1H), 8.07 (s, 1H).

EXAMPLE 7

1.1 g of N-hydroxysuccinimidoe ster of 2-(3-(5-methyl -6-methoxycarbony- 1-7-(3-nitrophenyl)-8-ethoxycarbonyl) -[3H,7H]thiazolo[3,4-a]pyridinyl)acetic acid are added to a solution of NH$_2$OH hydrochloride(0.14 g) and potassium bicarbonate (0.21 g) in DMF (10 ml). After 12 hrs stirring, the mixture is diluted with water and extracted repeatedly with AcOEt. The organic extracts are washed with water and dried over sodium sulphate. After evaporation of the solvent, the residue is crystallized from ethyl ether to give 0.75 g of 2-(3-(5-methyl-6-methoxycarbonyl-7-(3-nitrophenyl)-8-ethoxycarbonyl) [3 H,7 H]thiazolo[3,4-a]pyridinyl)-acetylhydroxylamine (m.p. 174°-175° C.).

EXAMPLE 8 a) 6.4 g of methy 1 2-(3-(5-methy 1-6-methoxycarbonyl -7-(3-nitrophenyl)-8-ethoxycarbonyl) [3 H,7 H]thiazolo [3,4-a]pyridinyl)acetate are added with stirring to a suspension of LiBr (3.8 g) and sodium borohydride (1.75 g) in diglyme (10 ml). The resulting solution is kept at room temperature for 30 minutes, and then heated for 1 hour at 50° C. The reaction mixture is poured into water and acidified with N HCl. After extraction with AcOEt, the organic extracts are washed repeatedly with water, dried ever sodium sulphate and evaporated to dryness to give 4.8 g of 2-(3-(5-methyl-6-methoxycarbonyl -7-(3-nitrophenyl)-8-ethoxycarbonyl) [3 H,7 H]thiazolo [3,4-a]pyridinyl)ethanol 1 H NMR (200 MHz) $\delta$1.36 (t, J=6.5 Hz, 3 H), 1.72 (br s, 1H), 1.96 (m, 1 H), 2.26 (m,1 H), 2.60 (s, 3 H), 3.70 (s, 3 H), 3.81 (m, 2 H), 4.16 (m, 2 H), 4.21 (d, J=18 Hz, 1 H), 4.67 (d, J=18 Hz, 1 H), 5.19 (s, 1 H), 5.64 (dd, J=5.10 Hz, 1 H), 7.40 (t, J=8 Hz, 1H), 7.62 (d, J=8 Hz, 1H), 8.02 (d, J=8 Hz, 1H), 8.05 (s, 1H).

b) triphenylphosphine (2.65 g) and carbon tetrabromide (7.2 g) are added at room temperature and with stirring to a solution of the compound obtained in a) (4.8 g) in dichloromethane (60 ml). After 5 hrs the mixture is evaporated to dryness and the residue is purified by silica gel column (120 g; eluant hexane/AcOEt 9/1, 2/1) to give, after crystallization from ethyl ether, 3.2 g of 2-(3-(5-methyl-6-methoxycarbonyl -7-(3-nitrophenyl)-8-ethoxycarbonyl)-[3H,7H]thiazolo[3,4-a]pyridinyl)ethylbromide (m.p. 181°-184° C.).

c) 0.4 g of potassium carbonate are added to a solution of the compound obtained in b) (1.26 g) and N- methylpiperazine (0,38 g ) in acetonitrile (20 ml). This suspension is kept at room temperature for 12 hrs with stirring, concentrated to a small volume, diluted with water and extracted repeatedly with dichloromethane. The organic extracts after usual work-up, are concentrated leading to 1.1 g of N-2-(3-(5-methyl-6-methoxycarbonyl -7-(3-nitrophenyl)-8-ethoxycarbonyl)-[3H,7H]-thiazolo [3,4-a]pyridinyl)-ethyl)-N'-methylpiperazine (hydrochloride, m.p. 220° C. with decomposition).

EXAMPLE 9

0.5 g of 2-mercapto-thiomethyl-3-ethoxycarbonyl-4-(3-nitrophenyl) -5-cyano-6-methyl-1,4-dihydropyridine are added under an inert gas atmosphere at room temperature and with stirring, to a solution of N-(2,6bis (pyrrolidin-1-yl) pyrimidin-4-yl)-N-propargyloylpiperazine (0.54 g) in DMF (5 ml). NaOH (0.12 g) is then added and stirring is continued for 24 hrs. The mixture is diluted with 1N HCl and extracted several times with AcOEt. The organic extracts are washed with water, dried over $Na_2SO_4$ and the solvent is evaporated under reduced pressure. After crystallization of the residue from hexane/AcOEt, 0.65 g of N-(2,6-bis(pyrrol idin-1yl) pyrimidin-4-yl)-N'-[2-(5-methyl-6-cyano-7-(3-nitrophenyl) -8-ethoxycarbonyl-acetyl]piperazine, m.p. 130°-132° C. are obtained.

EXAMPLE 10

0.6 g of 2- acetylthiomethyl-3-ethoxycarbonyl-4-(3-nitrophenyl) -5-cyano-6-methyl-1,4-dihydropyridine are added under an inert gas atmosphere at room temperature and with stirring, to a solution of N-(2,6-bis (pyrrolidin-1-yl)pyrimidin-4-yl)-N-propargyloyl piperazine (0.58 g) and triethylbenzylammonium chloride (0.1 g) in benzene (5 ml). 0.51 g of 35% NaOH are added and stirring is continued for 18 hrs, then the organic phase is separated, washed repeatedly with water and dried over $Na_2SO_4$. The solvent is then evaporated under reduced pressure. After crystallization of the residue from hexane/AcOEt, 0.6 g of N-(2,6-bis(-pyrrolidin-1-yl)pyrimidin-4-yl) -N'-[2-(3-(5-methyl-6-cyano-7-(3-nitrophenyl) -8-ethoxycarbonyl)acetyl]piperazine, m.p. 130°-132 ° C. are obtained.

EXAMPLE 11

A solution of 500 mg of N-(2,6-bis(pyrrolidin-1-yl)pyrimidin-4-yl) -N'-propargyloyl piperazine in benzene (1 ml) is added to a suspension of 0.5 g of S-[6-methyl -5-cyano-3-ethoxycarbonyl-4-(3-nitrophenyl)- 1,4-dihydropyridin-2-yl) methyl]isothioureide and 90 mg of triethylbenzylammonium chloride in 5 ml of benzene. 0.4 3 g of 35% NaOH are then added to this suspension.

Stirring is continued for 2 hrs, then the organic phase is separated, washed repeatedly with $H_2O$, and dried on $Na_2SO_4$. The solvent is then evaporated under reduced pressure leading to 0.7 g of N-(2,6-bis(pyrrolidin-1-yl) pyrimidin-4-yl) -N'-[2-(3-(5-methyl-6-cyano7-(3-nitrophenyl)-8-ethoxycarbonyl)acetyl] piperazine, m.p. 130°-132° C.

EXAMPLE 12 a) 0.6 g of methyl 2-(3-(5-methyl-6-allyloxycarbonyl -7-(3-nitrophenyl)-8-ethoxycarbonyl)[3 H,7 H]thiazolo[3,4-a]pyridinyl)acetate are added under an inert gas atmosphere, at room temperature and with stirring, to a suspension of 0.15 g of ammonium formate, 75 mg of triphenylphosphine and 0.13 mg of 10% Pd/C in 6 ml of dioxane. Stirring is continued for an hour; then the mixture is filtered on a Celite plug to eliminate the Pd/C, diluted with water and extracted repeatedly with AcOEt.

The organic extracts are treated with 5 ml of NaOH 1N. The basic aqueous phase thus obtained is subsequently neutralized with 2N HCl and extracted repeatedly with AcOEt.

The organic extracts are washed with $H_2O$, dried over $Na_2SO_4$ and the solvent is evaporated under reduced pressure, resulting in a residue (0.55 g) which is purified on silica gel column (14 g; eluant AcOEt-/AcOH 97/3) to give 0-5 g of methyl 2-(3-(5-methyl-6-carboxy-7-(3-nitrophenyl)-8-ethoxycarbonyl)[3H,7H]-thiazolo[3,4-a]pyridinyl)acetate.

b) 4-morpholinoethyl isonitrile (0.17 ml) is added dropwise to a solution, cooled to 0° C., of 0.14 g of N-hydroxysuccinimide and 0.45 g of the compound obtained in a) in THF (5 ml). When the addition is complete, the temperature is allowed to rise again to room temperature and stirring is continued for 2 hrs. The reaction mixture is then concentrated in a vacuum to 1/5 of the volume and, after dilution with N HCl, is extracted repeatedly with AcOEt. The organic extracts are washed with $H_2O$, dried over $Na_2SO_4$ and the solvent is evaporated under reduced pressure to give 0.52 g of methyl 2-(3-(5-methyl-6-(N-succinimidooxycarbonyl)-7-(3-nitrophenyl)-8-ethoxycarbonyl)[3H,7H]-thiazolo[3,4-a]pyridinyl)-acetate.

EXAMPLE 13

0.12 g of N-(3,6-bis-diethylaminopyridin-2-yl)piperazine are added at room temperature and with stirring, to a solution of 0.2 g of methyl 2-(3-(5-methyl -6(N-succinimidooxycarbonyl)-7-(3-nitrophenyl)-8-ethoxycarbonyl) [3H,7H]thiazolo[3,4-a]pyridinyl)acetate in 2 ml of DMF.

Stirring is continued for one hour, then the mixture is diluted with water and extracted repeatedly with AcOEt. The organic extracts are washed with $H_2O$, dried over $Na_2SO_4$ and evaporated under reduced pressure. The residue (0.24 g) is purified on silica gel column (8 g; eluant hexane/AcOEt 80/20) to give 0.21 g of N-(3,6-bis-diethylaminopyridin-2-yl )-N'-[(5-methyl-7-(3-nitrophenyl)-8-ethoxycarbonyl-3-methoxycarbonylmethyl -[3H,7H]thiazolo[3,4-a]pyridin-6-yl)carbonyl]-piperazine.

EXAMPLE 14

0.25 g of methyl 2-(3-(5-methyl-6-(N-succinimidooxycarbonyl) -7-(3-nitrophenyl)-8-ethoxycarbonyl)[3H,-7H]thiazolo[3,4-a]pyridinyl)acetate are added to a solution of $NH_2OH$ hydrochloride (30 rag) and $NaHCO_3$ (50 rag) in 3 ml DMF and stirred for 18 hrs. After dilution with $H_2O$, the mixture is extracted repeatedly with AcOEt. The organic extracts are washed with water and dried over $Na_2SO_4$.

After the solvent is evaporated, the residue (0.24 g) is purified on silica gel column (7 g, eluant AcOEt/hexane 50/50) to give 120 mg of N-[(5-methyl-7-(3-nitrophenyl)- 8-ethoxycarbonyl-3-methoxycarbonylmethyl -[3H,7H]thiazolo[3,4-a]pyridin-6-yl) carbonyl]hydroxylamine.

EXAMPLE 15

A solution of carbonyldiimidazole (0.7 g) in THF (5 ml), at room temperature and under an atmosphere of nitrogen, is added dropwise to a solution of 2-(3-(5-methyl -6-methoxycarbonyl-7-(3-nitrophenyl)-8-ethoxycarbonyl) [3H,7H]thiazolo[3,4-a]pyridinyl)ethanol (1.7 g) in THF (10 ml). Stirring is maintained for 6 hours, then a solution of N-(3,6-bis-diethylaminopyridin-2-yl)piperazine (1.16 g) in THF (8 ml) is added dropwise. The reaction mixture is kept at room temperature for 18 hrs, with stirring and then concentrated to a small volume. The residue is poured into water and extracted repeatedly with AcOEt (3×10 ml). The organic extracts are washed with water, dried over $Na_2SO_4$ and evaporated under reduced pressure, 2.9 g of crude product being obtained. By purification on silica gel column (80 g, eluant kexane/AcOEt 8/2),2.1 g of N-(3,6-bis-diethylaminopyridin -2-yl)-N'-(2-(3-(5-methyl-6-methoxycarbonyl -7-(3-nitrophenyl)-8-ethoxycarbonyl)[3H,7H]-thiazo [3,4-a]pyridinyl)ethoxycarbonyl)piperazine are obtained. $^1$H NMR (200 MHz) 0.95 (t, J=7.1 Hz, 6 H), 1.06 (t, J=7.1 Hz, 6 H), 1.28 (t, J=6.5 Hz, 3 H), 2.60 (s, 3 H), 2.96 (q, J=7.1, 4 H), 3.5 (m, 12 H), 3.68 (s, 3 H), 4.12 (m, 2 H), 4.20 (d, J=18 Hz, 1H), 4.30 (m, 2H), 4.69 (d, J=18 Hz, 1H), 5.20 (s, 1H), 5.50 (dd, J=10.4 Hz, 1H),6.05 (d, J=8 Hz, 1H),7.10 (d, J=8 Hz, 1H),7.41 (dd, J=7.8 Hz, 1H),7.60 (d, J=8 Hz, 1H), 8.02 (d, J=7 Hz, 1H),8.05 (s, 1H).

EXAMPLE 16

A mixture of ethyl 4-chloro-3-oxo-butanoate (57.3 ml), cyclohexylaldehyde (53.65 ml), acetic acid (2.75 ml) and benzylamine (4.38 ml) is kept for 24 hrs at room temperature. It is then diluted with 150 ml of ethyl acetate and washed with 100 ml of water, then with 100 ml of saturated sodium carbonate solution and finally with 100 ml of a saturated solution of $NaH_2PO_4$. The solvent is evaporated to give 108.43 g of 4-chloro3-oxo-2-ethoxycarbonyl-1-cyclohexyl-but-1-ene.

EXAMPLE 17 a) A solution of 4-chloro-3-oxo-2-ethoxycarbonyl1-cyclohexyl-but-1-ene (60 g) and methyl 3-amino crotonate (26.7 g) in acetonitrile (500 ml) is heated for 3 hrs at 60° C., cooled to 35° C. and then p-toluenesulphonic acid is added until pH 1 is reached. Stirring is continued for 30 minutes and the acetonitrile is evaporated. The mixture is treated with 300 ml of diethyl ether and 300 ml of water. The phases are separated and, after evaporation of the solvent and crystallization, 75.1 g of (±)-2-chloromethyl-3-ethoxycarbonyl -5-methoxycarbonyl-4-(cyclohexyl)-6-methyl-1,4-dihydropyridine (m.p. 103°–105° C.) are obtained.

b) A solution of 6 g of (±)-1,4-dihydropyridine obtained in a), thiourea (1.35 g) and ethanol (40 ml) is heated to reflux for 2 hrs.

After cooling, the crystalline precipitate of (±)-[(3-ethoxycarbonyl-5-methoxycarbonyl-4-(cyclohexyl)-6-methyl -1,4-dihydropyridin-2-yl)-methyl]-isothiouronium chloride (6.9 g, m.p. 201°–203° C.) is collected by filtration.

Following the same procedure, by reaction with thiourea of a 2-chloromethyldihydropyridine obtained from methyl 3-amino-crotonate and a suitable 1-substituted 4-chloro-3-oxo-2-ethoxycarbonyl-but-l-ene, the following compounds were obtained: (±)-[(3-ethoxycarbonyl-5-methoxycarbonyl-4-(cyclopropyl) -6-methyl-1,4-dihydropyridin-2-yl)-memethyl]-isothiouronium chloride; (±)-[(3-ethoxycarbonyl-5-methoxycarbonyl-4-(cyclobutyl) -6-methyl-1,4-dihydropyridin-2-yl)-memethyl]-isothiouronium chloride; (±)-[(3-ethoxycarbonyl-5-methoxycarbonyl-4-(cyclopentyl) -6-methyl-1,4-dihydropyridin-2-yl)-methyl]-isothiouronium chloride; (±)-[(3-ethoxycarbonyl-5-methoxycarbonyl-4-(cycloheptyl) -6-methyl-1,4-dihydropyridin-2-yl)-methyl]-isothiouronium chloride; (±)-[(3-ethoxycarbonyl-5-methoxycarbonyl-4-(3-methylsulphonamidophenyl) -6-methyl-1,4-dihydropyridin-2-yl) methyl]-isothiouronium chloride;

EXAMPLE 18

By reacting with thiourea the appropriate 2-chloromethyldihydropyridines, prepared using the process for preparing 3-amino-3-methylacrylonitrile or allyl 3-amino crotonate and the suitable 1-substituted 4-chloro-3-oxo-2-ethoxycarbonyl-1-butenes, the following compounds were prepared:

(±)-[(3-ethoxycarbonyl-5-cyano-4-(cyclopropyl)-6-methyl -1,4-dihydropyridin-2-yl)-methyl]-isothiouronium chloride;

(±)-[(3-ethoxycarbonyl-5-cyano-4-(cyclobutyl)-6-methyl 1,4-dihydropyridin-2-yl)-methyl]-isothiouronium chloride;

(±)-[(3-ethoxycarbonyl-5-cyano-4-(cyclopentyl)-6-methyl -1,4-dihydropyridin-2-yl)-methyl]-isothiouronium chloride;

(±)-[(3-ethoxycarbonyl-5-cyano-4-(cyclohexyl)-6-methyl 1,4-dihydropyridin-2-yl)-methyl]-isothiouronium chloride;

(±)-[(3-ethoxycarbonyl-5-cyano-4-(cyc 1 oheptyl)-6-methyl -1,4-dihydropyridin-2-yl)-methyl]-isothiouronium chloride;

(±)-[(3-ethoxycarbonyl-5-cyano-4-(3-methyl sulphonamidophenyl) -6-methyl-4-dihydropyridin-2-yl)-methyl]-isothiouronium chloride;

(±)-[(3-ethoxycarbonyl-5-carboallyloxy-4-(cyclopropyl) 6-methyl-1,4-dikydropyridin-2-yl)-methyl]-isothiouronium chloride;

(±)-[(3-ethoxycarbonyl-5-carboallyloxy-4-(cyclobutyl) -6-methyl-1,4-dihydropyridin-2-yl)-methyl]-isothiouronium chloride;

(±)-[(3-ethoxycarbonyl-5-carboallyloxy-4-(cyclopentyl) -6-methyl-1,4-dihydropyridin-2-yl)-methyl]-isothiouronium chloride;

(±)-[(3-ethoxycarbonyl-5-carboal lyl oxy-4-(cyclohexyl) -6-methyl-1,4-dihydropyridin-2-yl)-methyl]-isothiouronium chloride;

(±)-[(3-ethoxycarbonyl-5-carboa llyloxy-4-(cycloheptyl) -6-methyl-1,4-dihydropyridin-2-yl)-methyl]-isothiouronium chloride;

(±)-[(3-ethoxycarbonyl-5-carboallyloxy-4-(3-methylsulphonamidophenyl) -6-methyl-1,4-dihydropyridin-2-yl)-methyl ]-isothiouronium chloride;

EXAMPLE 19

Potassium bicarbonate (1.16 g) is added to a solution of (±)-[(3-ethoxycarbonyl-5-methoxycarbonyl-4-(cyclohexyl) -6-methyl-1,4-dihydropyridin-2-yl)-methyl]-isothiouronium chloride (5 g) in ethyl acetate (100 ml) and water (50 ml), at room temperature and with vigorous stirring, over a period of 30 minutes. The phases are separated and the aqueous phase is extracted with ethyl acetate (2×25 ml). The organic phases are washed with a saturated solution of NaCl and dried over $Na_2SO_4$. After evaporation of the solvent 3.6 g of (±)-[(3-ethoxycarbonyl-5-methoxycarbonyl-4- (cyclohexyl)-6-methyl -1,4-dihydropyridin-2-yl)-methyl]-isothiourea (m.p. 141°–143° C.) are obtained, by crystallization from Et$_2$O.

3.6 g of isothiourea thus obtained are heated to reflux in 500 ml of acetonitrile with 3.43 g of O,O'-dibenzoyl-D-tartaric acid for one hour. The mixture is then left at room temperature over night: 1.86 g of bis (+)-[(3-ethoxycarbonyl-5-methoxycarbonyl-4-(cyclohexyl) -6-methyl-1,4-dihydropyridin-2-yl)-methyl]isothiouronio -O,O'-dibenzoyl-D-tartrate (m.p. 158°–159° C.) crystallize. If the mother liquors are left over night at room temperature 1.92 g of (-)-[(3-ethoxycarbonyl -5-methoxycarbonyl-4-(cyclohexyl)-6-methyl-1,4-dihydropyridin -2-yl)-methyl]-isothiouronio-O,O'-dibenzoyl -D-tartrate (m.p. 174°–177° C.) crystallize.

The chiral isothioureas as the free bases are obtained from the chiral salts of isothiouronium by treatment with solutions of sodium bicarbonate in the same way as described at the beginning of this preparation. In this way the (+)-[(3-ethoxycarbonyl-5-methoxycarbonyl -4-(cyclohexyl)-6-methyl-1,4-dihydropyridin2-yl)-methyl]-isothiourea [α]D=+65° and the (-)-[(3ethoxy carbonyl-5-methoxy carbonyl-4-(cyclohexyl)-6-methyl -1,4-dihydropyridin-2-yl)-methyl]-isothiourea [α]D=−62° are obtained.

EXAMPLE 20

An aqueous solution of 35% NaOH (0.14 ml) is added, with stirring and under nitrogen atmosphere, to a solution of (+)-[(3-ethoxycarbonyl-S-cyano-4-(cyclopropyl) -6-methyl-1,4-dihydropyridin-2-yl)-methyl]-isothiouronium chloride (200 rag), triethylbenzylanlmonium chloride (30 rag) and N-(3,6-bisdiethylaminopyridin-2-yl) -N'-propargyloyl piperazine (160 rag) in benzene (2 ml) . Stirring is continued at room temperature for 90 minutes. The reaction mixture is concentrated under vacuum, diluted with water and extracted repeatedly with ethyl acetate (2×3 ml). The organic extracts are dried over sodium sulphate and the solvent is evaporated under reduced pressure. The residue is purified by silica gel column chromatography (9 g, eluant hexane/ethyl acetate 8/2) to obtain 250 mg of N-(3,6-bisdiethylaminopyridin-2-yl)-N'-[2-(5-methyl-8-ethoxycarbonyl -7-cyclopropyl -6-cyano)[3H,7H]-thiazolo[3,4-a]pyridin-3-yl) acetyl]piperazine.

In the same way, by reacting propargylamide with a suitable isothiouronium salt, the following products are prepared:

N-(3,6-bisdiethylaminopyridin-2-yl)-N'-[2-(5-methyl-6-(methoxycarbonyl-7-cyclopropyl-8-ethoxycarbonyl) -[3H, -7H]thiazolo[3,4-a]pyridin-3-yl) acetyl]piperazine;

N-(3,6-bisdiethylaminopyridin-2-yl)-N'-[2-(5-methyl-6-methoxycarbonyl -7-cyclobutyl-8-ethoxycarbonyl)-[3 H, 7H]thiazolo[3,4-a]pyridin-3-yl) acetyl]piperazine;

N-(3,6-bisdiethylaminopyridin-2-yl)-N'-[2-(5-methyl-6-methoxycarbonyl-7-cyclopentyl-8-ethoxycarbonyl)[3H,7H]-thiazolo[3,4-a]pyridin-3-yl)acetyl]piperazine;

N-(3,6-bis diethylaminopyridin-2-yl)-N'-[2-(5-methyl-6-methoxycarbonyl -7-cyclohexyl-8-ethoxycarbonyl)-[3H,-7H]thiazol [3,4-a]pyridin-3-yl) acetyl]piperazine [m.p. 172°–175° C.];

N-(3,6-bisdiethylaminopyridin-2-yl)-N'-[2-(5-methyl-6-methoxycarbonyl-7-cycloheptyl-8-ethoxycarbonyl)-[3H,7H]-thiazolo[3,4-a]pyridin-3-yl) acetyl]piperazine;

N-(3,6-bisdiethylaminopyridin-2-yl)-N'-[2-(5-methyl-6-methoxycarbonyl -7-(3-memethylsulphonamidophenyl)-8-ethoxycarbonyl) [3H,7H]thiazolo[3,4-a]pyridin-3-yl)acetyl]piperazine;

N-(3,6-bisdiethylaminopyridin-2yl)-N'-[2-(5-methyl-8-ethoxycarbonyl) -7-cyclobutyl-6-cyano)[3H,7H]-thiazolo[3,4-a]pyridin-3-yl)acetyl]piperazine;

N-(3,6-hisdie thylaminopyridin-2-yl)-N'-[2-(5-methyl-8-ethoxycarbonyl -7-cyclopentyl-6-cyano)[3H,7H]-thiazolo[3,4-a]pyridin-3-yl)acetyl]piperazine;

N-(3,6-bisdiethylaminopyridin-2-yl)-N'-[2-(5-methyl-8-ethoxycarbonyl -7-cyclohexyl-6-cyano)[3H,7H]-thiazolo[3,4-a]pyridin-3-yl)acetyl]piperazine;

N-(3,6-bisdiethylaminopyridin-2-yl)-N'-[2-(5-methyl-8-ethoxycarbonyl -7-cycloheptyl-6-cyano)[3 H, 7H]thiazolo[3,4-a]pyridin-3-yl)acetyl]piperazine;

N-(3,6-bisdiethylaminopyridin-2-yl)-N -[2-(5-methyl-8-ethoxycarbonyl -7-(3-methylsulphonamcylophenyl)-6-cyano)[3H,7H]thiazolo[3,4-a]pyridin-3-yl)acetyl]-piperazine;

N-(3,6-bisdiethylaminopyridin-2-yl)-N'-[2-(5-methyl-8-ethoxycarbonyl -7-cyclopropyl-6-carboallyloxy)-[3H,7H]-thiazolo[3,4-a]pyridin-3-yl)acetyl]piperazine;

N-(3,6-bisdiethylaminopyridin-2-yl)-N'-[2-(5-methyl-8-ethoxycarbonyl -7-cyclobutyl-6-carboallyloxy)-[3H,7H]thiazolo[3,4-a]pyridin-3-yl)acetyl]piperazine;

N-(3,6-hisdiethylaminopyridin-2-yl)-N'-[2-(5-methyl-8-ethoxycarbonyl -7-cyclopentyl-6-carboallyloxy)-[3H,7H]thiazolo[3,4-a]pyridin-3-yl)acetyl]piperazine;

N-(3,6-bisdiethylaminopyridin-2-yl)-N'-[2-(5-methyl-8-ethoxycarbonyl -7-cyclohexyl-6-carboallyloxy)-[3H,7H]thiazolo[3,4-a]pyridin-3-yl)acetyl]piperazine;

N-(3,6-bisdiethyiaminopyridin-2-yl)-N'-[2-(5-methyl-8-ethoxycarbonyl -7-cycloheptyl-6-carboal ly loxy)-[3 H, 7H]thiazolo[3,4-a]pyridin-3-yl)acetyl]piperazine;

N-(3,6-bisdiethylaminopyridin-2-yl)-N'-[2-(5-methyl-8-ethoxycarbonyl -7-(3-methylsulphonamidophenyl)-6-carboallyloxy) [3H, 7H]thiazolo[3,4-a]pyridin-3-yl)acetyl]piperazine;

N-(2,6-bis(pyrrolidin-1-yl) pyrimidin-4-yl)-N'-(2-(3-(5-methyl -6-allyloxycarbonyl-7-(3-chlorophenyl)-8-ethoxycarbonyl);

N-(2,6-bis(pyrrolidin-1-yl) pyrimidin-4-yl)-N'-(2-(3-(5-methyl -6-allyloxycarbonyl-7-(3-nitrophenyl)-8-ethoxycarbonyl);

N-2,6-bis(pyrrolidin-1-yl) pyrimidin-4-yl)-N'-(2-(3-(5-methyl -6-allyloxycarbonyl-7-cyclohexyl-8-ethoxycarbonyl);

N-(4,6-bis(pyrrolidin-1-yl)-1,3,5-triazin-2-yl)-N'-(2-(3-(5-methyl-6-allyloxycarbonyl-7-(3-chlorophenyl)-8ethoxycarbonyl);

N-(4,6-bis(pyrrolidin-1-yl)-1,3,5-triazin-2-yl)-N'-(2-(3-(5-methyl-6-allyloxycarbonyl-7-(3-nitrophenyl)-8-ethoxycarbonyl);

N-(4,6-bis(pyrrolidin-1-yl)-1,3,5-triazin-2-yl)-N'-(2-(3-(5-methyl-6-allyloxycarbonyl-7-cyclohexyl)-8-ethoxycarbonyl);

N-(3,6-bis(diethylamino)pyridin-2-yl)-N'-(2-(3-(5-methyl -6-allyloxycarbonyl-7-(3-chlorophenyl)-8-ethoxycarbonyl);

N-(3,e-bis(diethylamino)pyridin-2-yl)-N'-(2-(3-(5-methyl -6-allyloxycarbonyl-7-(3-nitrophenyl)-8-ethoxycarbonyl).

EXAMPLE 21 a) 10 g of (±)-[(3-ethoxycarbonyl-5-methoxycarbonyl -4-(cyclohexyl)-6-methyl-1,4-dihydropyridin-2-yl)-methyl -isothiouronium chloride are dissolved in 200 ml of methanol together with 1.8 ml of methyl propiolate and 3.6 ml of 35% NaOH. After 20 minutes the solution is concentrated under reduced pressure and at room temperature, to half volume. By standing 9.8 g of 3-[(3-ethoxycarbonyl-5-methoxycarbonyl-4-(cyclohexyl)-6methyl) -1,4-dihydropyridin-2-yl]-methylthiomethyl acrylate (m.p. 188°–190° C.] are obtained.

b) 1.83 ml of DBU are added dropwise to a solution of 5 g of the compound obtained in a). After 24 hrs the reaction is complete, with the formation of a crystalline product which is separated by filtration. 4.9 g of methyl 2-(3-(5-methyl-6-methoxycarbonyl-7-cyclohexyl -8-ethoxycarbonyl)[3H,7H]thiazolo[3,4-a]pyridinyl)acetate, m.p. 132°–134° C., are obtained.

EXAMPLE 22 a) 1.5 g of 2-(3-(5-methyl-6-methoxycarbonyl-7-(3-nitrophenyl) -8-ethoxycarbonyl)[3H,7H]thiazolo[3,4-a]pyridinyl)ethanol, 6.28 ml of 1.8 M solution of $HN_3$ in benzene and 1.64 g of triphenylphosphine are dissolved in 8 ml of benzene. After cooling to 0° C., a solution of 0.94 ml of diethylazadicarboxylate in 2 ml of benzene is added to the reaction mixture which is left in nitrogen atmosphere, with stirring and at room temperature for 1 hr . 1 N NaOH is then added until a basic pH is reached; the organic phase is separated, washed with water (3×15 ml) and dried over sodium sulphate. The solvent is avaoorated under reduced pressure and the crude reaction product (3.2 g) is purified on silica gel column (90 g of silica; eluant chloroform), leading to 910 mg of 2-(3-(5-methyl-6-methoxycarbonyl7-(3-nitrophenyl)-8-ethoxycarbonyl)[3H,7H]thiazolo[3,4a]pyridinyl)ethylazide, m.p. 155°–157° C.

b) 0.9 g of 2-(3-(5-methyl-6-methoxycarbonyl-7-(3-nitrophenyl) -8-ethoxycarbonyl)[3H, 7H]thiazolo[3,4-a]pyridinyl)ethylazide and 0.4 ml of triethylphosphite are dissolved in 9 ml of benzene. After 24 hrs at room temperature and with stirring, the reaction mixture is saturated with gaseous HCl. After 48 hrs 900 mg of 2-(3-(5-methyl-6-methoxycarbonyl-7-(3-nitrophenyl)-8-ethoxycarbonyl) [3H 7H]thiazolo[3,4-a]pyridinyl)-ethylamine hydrochloride, m.p. 118°–121 ° C. are obtained after filtration.

c) 0.9 g of the compound obtained in b) are suspended in 10 ml of ethyl acetate. 10 ml of saturated NaHCO3 solution are added. The resulting suspens ion is stirred for 20 minutes, then the organic phase is separated and dried over sodium sulphate. The solvent is evaporated under reduced pressure to give 0.8 g of 2-(3-(5-methyl-6-methoxycarbonyl-7-(3-nitrophenyl)-8-ethoxycarbonyl) [3H,7H]thiazolo[3,4-a]pyridinyl)-ethylamine.

EXAMPLE 23

0.3 g of 2-(3-(5-methyl-6-methoxycarbonyl-7-(3-nitrophenyl) -8-ethoxycarbonyl)[3H,7H]thiazolo[3,4-a]pyridinyl)ethylamine are dissolved in 3 ml of THF; 132 mg of thiocarbonyidiimidazole are added to the solution. This left at room temperature and with stirring for 2 hrs, then a solution of 220 mg of N-(3,6-bisdiethylaminopyridin-2-yl)piperazine in 3 ml of THF is added dropwise. After another 3 hrs water is added to the reaction mixture which is then extracted with ethyl acetate (3×3 ml) . The organic phase is separated, washed with water (3×5 ml) and dried over sodium sulphate. The solvent is evaporated under reduced pressure to give 170 mg of crude product. By purification of this latter on silica gel column (5 g of silica; eluant hexane/ethyl acetate 80/25) 120 mg of N-(3,6-bisdiethylaminopyridin-2-yl)-N'-(2-(3-(5-methyl-6-methoxycarbonyl -7-(3-nitrophenyl)-8-ethoxycarbonyl)[3H, 7H]thiazolo[3,4-a]pyridinyl) -ethylaminothiocarbonyl)-piperazine, (m.p. 110°–130° C. with decomposition), are obtained.

EXAMPLE 24 a) 1 g of 2-(3-(5-methyl-6-methoxycarbonyl-7-(3-nitrophenyl) -8-ethoxycarbonyl)[3H,7H]thiazolo[3,4-a]pyridinyl) acetic acid is dissolved in 10 ml of anhydrous THF. 380 mg of carbonyldiimidazole are added. After 1 hr at room temperature, under stirring and under nitrogen atmosphere, 283 mg of dimethylaminopyridine and 34 0 mg of Meldrum acid are added. The mixture is heated to 60° C. for 2 hrs, and then concentrated. 20 ml of 0.1 N HCl are added. The mixture is extracted with AcOEt (3×10 ml). The organic phase is separated and washed with 0.1 N NaOH (3×10 ml) and dried over sodium sulphate. The solvent is evaporated under reduced pressure to give 970 mg of crude product which is recrystallized from acetonitrile. After filtration, 900 mg of enolate with m.p. 190°–193° C. are obtained.

b) 900 mg of the oroducn obtained in a) are suspended in 10 ml of ethyl acetate. 10 ml of 0.1 N HCl are added and stirred for 20 minutes; then the organic phase is separated and dried over sodium sulphate. The solvent is evaporated under reduced pressure to give 850 mg of 1-(2,2-dimethyl-4,6-dioxo-l,3-dioxan-5-yl)-2-(3-(5-methyl-6-methoxycarbonyl-7-(3-nitrophenyl)-8-ethoxycarbonyl) [3H,7H]thiazolo[3,4-a]pyridin-2-yl)-ethan-1-one.

EXAMPLE 25

630 mg of 1-(2,2-dimethyl-4,6-dioxo-l,3-dioxan-5-yl) -2-(3-(5-methyl-6-methoxycarbonyl-7-(3-nitrophenyl)-8-ethoxycarbonyl)[3H,7H]thiazolo[3,4-a]pyridinyl)-ethan-1-one and 200 mg of p-toluenesulphonic acid are dissolved in 10 ml of methanol; thisis stirred for 4 hrs and then the reaction mixture is concentrated, 10 ml of a saturated NaHCO3 solution are added. The mixture is extracted with AcOEt (3×10 ml),the organic phase is separated and washed with water (3×10 ml) and dried over sodium sulphate. The solvent is evaporated under reduced pressure to give 550 mg of crude product. After purification on silica gel column (15 g of silica; eluant methylene chloride/ethyl acetate 95/5) 540 mg of methyl 4-(3-(5-methyl-6-methoxycarbonyl-7-(3-nitrophenyl) -8-ethoxycarbonyl)[3H,7H]thiazolo[3,4-a]pyridinyl) -3-oxobutanoate are obtained; $^1$H NMR (200 MHz) 1.28 (t, J=6.5 Hz, 3 H), 2.60 (s, 3 H), 3.3 (d, J=7 Hz, 2 H), 3.55 (m, 2 H), 3.70 (s, 3 H), 3.77 (s, 3 H), 4.18 (m, 2 H), δ 4.25 (d, J=18 Hz, 1H), 4.62 (d, J=18 Hz, 1 H), 5.20 (s, 1H), 5.80 (t, J=7 Hz, 1H), 7.42 (t, J=8 Hz, 1H), 7.64 (d, J=8 Hz, 1H), 8.00 (s, 1H), 8.05 (d, J=B Hz, 1H).

EXAMPLE 26

500 g of 1-(2,2-dimethyl-4,6-dioxo-1,3-dioxan-5-yl) -2-(3-(5-methyl-6-methoxycarbonyl-7-(3-ni trophenyl)-8-ethoxycarbonyl)-[3H,7H]thiazolo[3,4-a]pyridinylethan-1-one are dissolved in 10 ml of acetonitrile, to which are added 200 mg of 2-aminopyridine and 160 mg of p-toluenesulphonic acid. The reaction mixture is refluxed for 1 hour and concentrated. 10 ml of 0.1 N HCl are added, the resulting mixture is extracted with AcOEt (3×10 ml) and the organic phase is washed with a saturated NaHCO$_3$ solution, then dried over sodium sulphate. The solvent is evaporated under reduced pressure to give 450 mg of crude product. By purification on silica gel column (15 g of silica; eluant hexane/ethyl acetate 1/1). 400 mg of N-[4-(3-(5-methyl -6-methoxycarbonyl-7-(3-nitrophenyl)-8-ethoxycarbonyl) [3H,7H]thiazolo[3,4-a]pyridinyl)-3-oxobutanoyl]-2-aminopyridine are obtained; 1H NMR (200 MHz) δ 1.28 (t, J=6.5 Hz, 3 H),2.60 (s, 3 H),3.34 (d, J=7 Hz, 2 H),3.67 (s, 5 H),4.15 (m, 2 H),4.25 (d, J=18 Hz, 1 H),4.62 (d, J=18 Hz, 1 H),5.20 (s, 1 H),5.80 (t, J=7 Hz, 1H),7.09 (dd, J=5.7 Hz, 1H),7.42 (t, J=8 Hz, 1 H), 7.64 (d, J=8 Hz, 1H), 7.72 (t, J=5 Hz, 1H), 8.00 (s, 1H) ? 8.05 (d, J=8 Hz, 1H),8.18 (m, 1H),8.30 (m, 1H),9.22 (br s, 1H) .

EXAMPLE 27

A solution of N-hydroxysuccinimide (172 rag) and 300 mg of anti-2-(3-(5-methyl-6-methoxycarbonyl-7-(3-nitrophenyl) -8-ethoxycarbonyl)-[3 H, 7H]thiazolo[3,4-a]-pyridinyl)-acetic acid in tetrahydrofurane (THF, ml 5) is cooled to 0° C. and 4-morpholinoethylisonitrile (0.13 ml) is added under stirring thereto. The mixture is kept for 30 minutes at room temperature, poured into an excess of N HCl, and extracted with AcOEt. The organic extracts are evaporated to dryness, leading to 0.7 mM of crude N-hydroxysuccinimido ester of the anti-2-(3-(5-methyl-6-methoxycarbonyl-7-(3-nitrophenyl)-8-ethoxycarbonyl) -[3H,7H]thiazolo[3,4-a]pyridinyl)acetic acid. This latter is dissolved in DMF (5 ml) and to this solution are added 194 mg of N-(2,6-bisdiethylaminopyridin-2-yl)-piperazine. The mixture is kept at room temperature for 1 hr, diluted copiously with water and extracted with AcOEt. After the usual work-up of the organic phase and purification of the residue on silica gel column (15 g of silica; eluant hexane/ethyl acetate 1/1). 360 mg of anti-N-(2,6-bisdiethylaminopyridin-2-yl) -N'-(2-(3-(5-methyl-6-methoxycarbonyl-7-(3-nitrophenyl) -8-ethoxycarbonyl)-[3H, 7H]thiazolo[3,4-a]pyridinyl) -acetyl)-piperazine are obtained; $^1$H NMR (200 MHz) δ0.93 (t, J=7.1 Hz, 6H),1.08 (t, J=7.1 Hz, 6H),1.20 (t, J=6.5 Hz, 3H),2.57 (s, 3H),2.8 (dd, J=15.2 Hz, 1H),2.96 (q, J=7.1, 4H),3.02 (dd, J=11.15 Hz, 1H) , 3.4–3.8 (m, 12H), 3.60 (s, 3H), 4.15 (m, 2H), 4.17 (d, J=18 Hz, 1H),4.66 (d, J=18 Hz, 1H),5.08 (s, 1H),5.33 (dd, J=11.2 Hz, 1H),6.07 (d, J=8 Hz, 1H),7.10 (d, J=8 Hz, 1H),7.45 (dd, J=7.8 Hz, 1H),7.61 (d, J=8Hz, 1H) , 8.02 (d, J=7Hz, 1H), 8,12 (s, 1H).

In accordance with the procedure of example 12-(a), the following ((6-carboxy-[3H,7H]thiazolo[3,4-a]pyridinyl)acetyl)piperazines were obtained: N-(2,6-bis(pyrrolidin-1-yl) pyrimidin-4-yl)-N'-(2-(3-(5-methyl -7-(3-chlorophenyl)-8-ethoxycarbonyl); N-(2,6-bi s (pyrrolidin-1-yl) pyrimidin-4-yl)-N'-(2-(3-(5-methyl -7-(3-nitrophenyl)-8-ethoxycarbonyl); N-(2,6-bis(pyrrolidin-1-yl) pyrimidin-4-yl)-N'-(2-(3-(5-methyl -7-cyclohexyl-8-ethoxycarbonyl); N-(4,6-hi s (pyrrolidin-1-yl)-1,3,5-triaz in-2-yl)-N'-(2-(3-(5-methyl-7-(3-chlorophenyl)-8-ethoxycarbonyl); N-(4,6-bis(pyrrolidin-1-yl)-1,3,5-triazin-2-yl)-N'-(2-(3-(5-methyl-7-(3-nitrophenyl)-8-ethoxycarbonyl); N-(4,6-bis(pyrrolidin-1-yl)-1,3,5-triazin-2-yl)-N'-(2-(3-(5-methyl-7-cyclohexyl)-8-ethoxycarbonyl); N-(3,6-bis(diethylamino)pyridin-2-yl)-N'-(2-(3-(5-methyl -7-(-3-chlorophenyl)-8-ethoxycarbonyl); N-(3,6-bis(diethylamino)pyridin-2-yl)-N'-(2-(3-(5-methyl -7-(-3-nitrophenyl)-8-ethoxycarbonyl); N-(3,6-bis(diethylamino)pyridin-2-yl)-N'-(2-(3-(5-methyl -7-cyclohexyl-8-ethoxycarbonyl) .

EXAMPLE 29

To a mixture of 300 mg of N-(2,6-bis(pyrrolidin-1-yl)pyrimidin-4-yl) -N'-(2-(3-(5-methyl-6-carboxy-7-(3chlorophenyl) -8-ethoxycarbonyl[3H,7H]-thiazolo[3,4-a]pyridinyl)acetyl) piperazine in THF (3 ml) is added under an inert gas atmosphere, at room temperature and with stirring, carbonyldiimidazole (75 rag). After 3 hr to the reaction mixture is added dropwise a solution of 0,26 ml of 2-(N-pyrrolidin)ethylamine in THF (1 ml) and the stirring is continued for 5 hr, then it is diluted with 20 ml of water and extracted repeatedly with AcOEt.

The organic extracts are washed with water (3×10 ml), dried over Na$_2$SO$_4$ and the solvent is evaporated under reduced pressure, resulting in a residue (0,5 g) which is purified on silica gel column (13 g; eluant AcOEt 95/triethylamine 5) to give 0,3 g of N-(2,6-bis (pyrrolidin-1-yl)pyrimidin-4-yl)-N'-(2-(3-(5-methyl6-(2-(N-pyrrolidin) ethylaminocarbonyl)-7-(3-chlorophenyl) -8-ethoxycarbonyl[3H,7H]thiazolo[3,4-a]pyridinyl-)acetyl)piperazine.

Analogously the following 6-(2-(N-pyrrolidin)ethylaminocarbonyl) [3H,7H]thiazolo[3,4-a]pyridinyl)acetyl) piperazines were prepared:
N-(2,6-bis(pyrrolidin-1-yl) pyrimidin-4-yl)-N'-(2-(3-(5-methyl -7-(3-nitrophenyl)-8-ethoxycarbonyl);
N-(2,6-bis(pyrrolidin-1-yl)pyrimidin-4-yl)-N'-(2-(3-(5-methyl -7-cyclohexyl-8-ethoxycarbonyl);
N-(4,6-bis(pyrrolidin-1-yl)-1,3,5-triazin-2-yl)-N'-(2-(3-(5-methyl-7-(3-chlorophenyl)-8-ethoxycarbonyl);
N-(4,6-bis(pyrrolidin-1-yl)-1,3,5-triazin-2-yl)-N'-(2 -(3-(5-methyl-7-(3-nitrophe nyl)-8-ethoxycarbonyl);
N-(4,6-bis(pyrrolidin-1-yl)-1,3,5-triazin-2-yl)-N'-(2-(3-(5-methyl-7-cyclohexyl-8-ethoxycarbonyl)
N-(3,6-bis(diethylamino)pyridin-2-yl)-N'-(2-(3-(5-methyl -7-(3-chlorophenyl)-8-ethoxycarbonyl);
N-(3,6-bis(diethylamino) pyridin-2-yl)-N'-(2-(3-(5-methyl -7-(3-nitrophenyl)-8-ethoxycarbonyl)
N-(3,6-bis(diethylamino)pyridin-2-yl)-N'-(2-(3-(5-methyl -7-cyclohexyl-8-ethoxycarbonyl).

EXAMPLE 30

In accordance with the procedure of example 8a and 15, the following (([3H,7H]thiazolo[3,4-a]pyridinyl)ethoxycarbonyl)piperazines were obtained: (7R)-N-(2,6-bis(pyrrolidin-1-yl) pyrimidin-4-yl)-N'-(2-(3-(5-methyl-6-methoxycarbonyl-7-(3-nitrophenyl)-8-ethoxycarbonyl), sulfate, m.p. 122°–126° C.; (7R)-N-(3,6-bis(diethylamino)pyridin-2-yl)-N'-(2-(3-(5-methyl -6-methoxycarbonyl-7-(3-nitrophenyl)-8-ethoxycarbonyl), hydrochloride, m.p. 110°–115° C.,[α]$_D$= +29.2° (c=0.2% in DMF);
N-(4,6-bis(pyrrolidin-1-yl)-1,3,5-triazin-2-yl)-N'-(2-(3-(5-methyl-6-methoxycarbonyl-7-(3-nitrophenyl)-8-ethoxycarbonyl);
N-(2,6-bis(pyrrolidin-1-yl)pyrimidin-4-yl)-N'-(2-(3-(5-methyl -6-methoxycarbonyl-7-(3-chlorophenyl)-8-ethoxycarbonyl);
N-(3,6-bis(diethylamino) pyridin-2-yl)-N'-(2-(3-(5-methyl -6-methoxycarbonyl-7-(3-chlorophenyl)-8-ethoxycarbonyl);
N-(4,6-bis(pyrrolidin-1-yl)-1,3,5-triazin-2-yl)-N'-(2-(3-(5-methyl-6-methoxycarbonyl-7-(3-chlorophenyl)-8ethoxycarbonyl);

N-(2,6-bis(pyrrolidin-1-yl)pyrimidin-4-yl)-N'-(2-(3-(5-methyl -6-methoxycarbonyl-7-cyclohexyl-8-ethoxycarbonyl);

N-(3,6-bis(diethylamino)pyridin-2-yl)-N'-(2-(3-(5-methyl -6-methoxycarbonyl-7-cyclohexyl-8-ethoxycarbonyl);

N-(4,6-bis(pyrrolidin-1-yl)-1,3,5-triazin-2-yl)-N'-(2-(3-(5-methyl-6-methoxycarbonyl-7-cyclohexyl-8-ethoxycarbonyl), N-(2,6-bis(pyrrolidin-1-yl)pyrimidin-4-yl)-N'-(2-(3-(5-methyl -6-allyloxycarbonyl-7-(3-nitrophenyl)-8-ethoxycarbonyl))), N-(3,6-bis(diethylamino)pyridin-2-yl)-N'-(2-(3-(5-methyl -6-allyloxycarbonyl-7-(3-nitrophenyl)-8-ethoxycarbonyl))), N-(4,6-bis(pyrrolidin-1-yl)-1,3,5-triazin-2-yl)-N,-(2-(3-(5-methyl-6-allyloxycarbonyl-7-(3-nitrophenyl)-8ethoxycarbonyl))), N-(2,6-bis(pyrrolidin-1-yl)pyrimidin-4-yl)-N'-(2-(3-(5-methyl -6-allyloxycarbonyl-7-(3-chlorophenyl)-8-ethoxycarbonyl))), N-(3,6-bis(diethylamino)pyridin-2-yl)-N'-(2-(3-(5-methyl -6-allyloxycarbonyl-7-(3-chlorophenyl)-8-ethoxycarbonyl))), N-(4,6-bis(pyrrolidin-1-yl)-1,3,5-triazin-2-yl)-N'-(2-(3-(5-methyl-6-allyloxycarbonyl-7-(3-chlorophenyl)-8ethoxycarbonyl))), N-(2,6-bis(pyrrolidin-1-yl)pyrimidin-4-yl)-N'-(2-(3-(5-methyl -6-allyl oxycarbonyl-7-cyclohexyl-8-ethoxycarbonyl))), N-(3,6-bis(diethylamino) pyridin-2-yl)-N'-(2-(3-(5-methyl -6-allyloxycarbonyl-7-cyclohexyl-8-ethoxycarbonyl))), N-(4,6-bis(pyrrolidin-1-yl)-1,3,5-triazin-2-yl)-N'-(2-(3-(5-methyl-6-allyloxycarbonyl-7-cyclohexyl)-8-ethoxycarbonyl))), N-(2,6-bis(pyrrolidin-1-yl)pyrimidin-4-yl)-N'-(2-(3-(5-methyl -6-methoxycarbonyl-7-phenyl-8-ethoxycarbonyl))), N-(3,6-bis(diethylamino)pyridin-2-yl)-N'-(2-(3-(5-methyl -6-methoxycarbonyl-7-phenyl-8-ethoxycarbonyl))), N-(4,6-bis(pyrrolidin-1-yl)-1,3,5-triazin-2-yl)-N'-(2-(3-(5-methyl-6-methoxycarbonyl-7-phenyl-8-ethoxycarbonyl))), N-(2,6-bis(pyrrolidin-1-yl)pyrimidin-4-yl)-N'-(2-(3-(5-methyl -6-methoxycarbonyl-7-(2,3-dichlorophenyl)-8-ethoxycarbonyl))), N-(3,6-bis(diethylamino)pyridin-2-yl)-N'-(2-(3-(5-methyl -6-methoxycarbonyl-7-(2,3-dichlorophenyl)-8-ethoxycarbonyl))), N-(4,6-bis(pyrrolidin-1-yl)-1,3,5-triazin-2-yl)-N'-(2-(3-(5-methyl-6-methoxycarbonyl-7-(2,3-dichlorophenyl)-8-ethoxycarbonyl))).

EXAMPLE 31

Following the procedure of example 12-(a), 750 mg of N-(2,6-bis(pyrrolidin-1-yl)pyrimidin-4-yl)-N'-(2-(3-(5-methyl-6-allyl oxycarbonyl-7-(3-chlorophenyl)-8-ethoxycarbonyl) [3H,7H]thiazolo[3,4-a]pyridinyl)ethoxycarbonyl)piperazine are converted into 670 mg of N-(2,6-bis(pyrrolidin-1-yl)pyrimidin-4-yl)-N'-(2-(3-(5-methyl -6-carboxy-7-(3-chlorophenyl)-8-ethoxycarbonyl[3H,7H]thiazolo[3,4-a]pyridinyl) ethoxycarbonyl)piperazine.

A solution of 650 mg of the latter compound in THF (6 ml) is added with 160 mg of carbonyl diimidazole and left at room temperature, with stirring and under an inert gas atmosphere, for 3 hours; then the reaction mixture is added with 0.52 ml of 2-(N-pyrrotidin)ethylamine and the stirring is continued for 20 hours. The reaction mixture is diluted with 20 ml of water and extracted repeatedly with AcOEt. The organic extracts are washed with water (3×10 ml), dried over $Na_2SO_4$ and the solvent i s evaporated under reduced pressure, resulting in a residue (0.8 g) which is purified on silica gel column (25 g; eluant AcOEt/triethylamine 95/5) to give 0.55 g of N-(2,6-bis(pyrrolidin-1-yl) pyrimidin-4-yl)-N'-(2-(3-(5-methyl -6-(2-(N-pyrrolidin)ethylaminocarbonyl)-7-(3-chlorophenyl) -8-ethoxycarbonyl)[3H,7H]thiazolo[3,4-a]pyridinyl)ethoxycarbonyl)piperazine.

EXAMPLE 32

In accordance with the procedure of example 31, the following (6-(2-(N-pyrrolidin)ethylaminocarbonyl)[3H,7H]thiazolo[3,4-a]pyridinyl)ethoxycarbonyl)piperazines were prepared:

N-(2,6-bis(pyrrolidin-1-yl) pyrimidin-4-yl)-N'-(2-(3-(5-methyl -7-(3-nitrophenyl)-8-ethoxycarbonyl))), N-(3,6-bis(diethylamino)pyridin-2-yl)-N'-(2-(3-(5-methyl -7-(3-nitrophenyl)-8-ethoxycarbonyl))), N-(4,6-bis(pyrrolidin-1-yl)-1,3,5-triazin-2-yl)-N'-(2-(3-(5-methyl-7-(3-nitrophenyl)-8-ethoxycarbonyl))), N-(3,6-bis(diethylamino)pyridin-2-yl)-N'-(2-(3-(5-methyl -7-(3-chlorophenyl)-8-ethoxycarbonyl))), N-(4,6-bis(pyrrolidin-1-yl)-1,3,5-triazin-2-yl)-N'-(2-(3-(5-methyl-7-(3-chlorophenyl)-8-ethoxycarbonyl))), N-(2,6-bis(pyrrolidin-1-yl)-pyrimidin-4-yl)-N'-(2-(3-(5-methyl-7-cyclohexyl-8-ethoxycarbonyl))), N-(3,6-bis(diethylamino)-pyridin-2-yl)-N'-(2-(3-(5-methyl -7-cyclohexyl-8-ethoxycarbonyl))), N-(4,6-bis(pyrrolidin-1-yl)-1,3,5-triazin-2-yl)-N'-(2 -(3-(5-methyl-7-cyclohexyl-8-ethoxycarbonyl))).

We claim:

1. Compounds of formula (I)

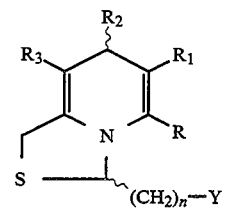

in which:

R is $(C_1-C_4)$ alkyl;

$R_1$ is a cyano, free or salified carboxyl, $C_1-C_6$ alkoxycarbonyl, hydroxyaminocarbonyl group or a carboxyamide group of the formula

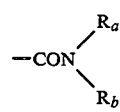

wherein Ra and

Rb are as defined below or a group of the formula

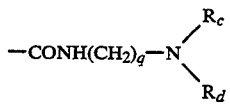

wherein q is an integer from 2 to 4;

R$_c$ is hydrogen, (C$_1$-C$_6$) alkyl, benzyl; Rd is hydrohydrogen or (C$_1$-C$_6$) alkyl or Rc and Rd, taken together with the nitrogen atom, form a pyrrolidine, piperidine, morpholine, thiomorpholine, (C$_1$-C$_4$) alkylpiperazine; R$_2$ is a (C$_3$-C$_7$) cycloalkyl group, α, β or γ-pyridyl, a phenyl group optionally containing from 1 to 3 substituents selected from the group consisting of (C$_1$-C$_4$) alkyl; (C$_1$-C$_4$) alkoxy; (C$_1$-C$_4$) alkylthio; phenoxy; 4-hydroxyhenoxy; phenylthio; 4-hydroxyhenylthio; halogen atoms; cyano, azido, nitro, amino, (C$_1$-C$_6$) acylamino, trihaloacetylamino; methaneor trifluoromethanesulphonamido, benzene-or paratolyl-sulphonamido, trihalomethyl, dihalomethoxy groups, a free or salified carboxy group and (C$_1$-C$_4$) alkoxycarbonyl or a bicyclic ring selected from the group con sis ting of benzo-1,3-dioxolan-4-yl, 1,4-benzodioxolan-6-yl, 1,4-benzodioxolan-5-yl, benzofuran-4-yl or benzofurazan-4-yl; R$_3$ is a free or salified carboxy group, a C$_1$-C$_6$ alkoxycarbonyl group or a —CONR$_a$R$_b$ or

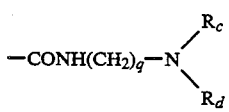

group as defined above;

Y is one of the following groups: COOX; —NHCOA; —NCO; —COA; —CONHOR$_e$; —OCOA; A; —CO—CH$_2$—CO—R$_f$; —NHCSA;

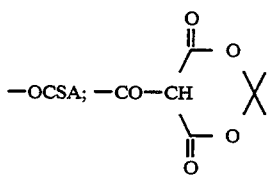

R$_e$ is hydrogen, (C$_1$-C$_6$) alkyl, phenyl or benzyl ring optionally substituted as above;

R$_f$ is (C$_1$-C$_6$) alkoxy,

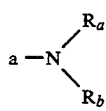

group wherein R$_a$ and

R$_b$ are as defined below or a (pyridin-2-yl)amino group;

X is hydrogen, (C$_1$-C$_4$) alkyl, allyl, propargyl or an N-succinimidyl group of formula

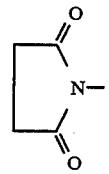

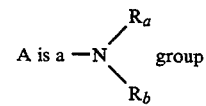

wherein R$_a$ or R$_b$, which are the same or different, are hydrogen, (C$_1$-C$_4$) alkyl, allyl, propargyl, (C$_3$-C$_7$) cycloalkyl, phenyl ring optionally substituted as above, benzyl unsubstituted or substituted by hydroxy and/or methoxy groups, benzhydryl unsubstituted or substituted by halogens or, taken together with the nitrogen atom, they form an aziridine, azetidine group or a ring of formula

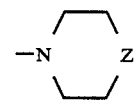

wherein Z is O, S, CH$_2$ or —S—S— or a ring of formula

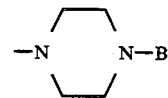

wherein B is hydrogen, (C$_1$-C$_4$) alkyl, benzyl unsubstituted or substituted by hydroxy and/or C$_1$-C$_4$ alkoxy groups, benzhydryl unsubstituted or substituted by halogen atoms, unsubstituted or as above substituted phenyl, pyridin-2-yl pyrimidin-4-yl, pyrimidin-2-yl or 1,3,5-triazinyl-2-yl, optionally substituted by 1 or 2 amino groups such as amino, methylamino, ethylamino, 2-propenylamino, 2 propynylamino, propylamino, isopropylamino or dialkylamino such as dimethylamino, diethylamino, ethylallylamino, piperidin-1-yl, morpholin-4-yl, pyrrolidin-1-yl groups;

n is the integer 1 or 2, their salts, enantiomers, diastereoisomers or racemic mixtures.

2. Compounds according to claim 1 in which the R$_1$ and R$_3$ groups are (C$_1$-C$_6$) alkoxycarbonyl groups.

3. Compounds according to claim 1 in which the R$_2$ group is a phenyl group as defined in claim 1.

4. Compounds according to claim 1 in which n is 1 or 2 and Y is a —COA, —OCOA or A group, where A is as defined in claim 1.

5. Compounds according to claim 1 in which A is a 1-aziridinyl, 1-azetidinyl, 1-pyrrolidinyl, 1-piperidinyl, 4-morpholinyl, 4-thiamorpholinyl group, a ring of formula

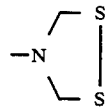

or a group of formula

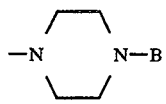

wherein B is as defined in claim 1.

6. A process for preparing the compounds of formula I which consists in reacting a Michael acceptor of formula (IIa) or (IIb):

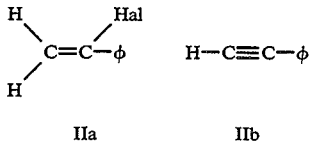

wherein Hal is an halogen atom (chlorine, bromine or iodine) and the symbol $\phi$ is a carboxyester, chlorocarbonyl, cyano, azidocarbonyl

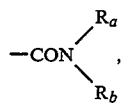

($C_1$-$C_4$) alkylcarbonyl, benzoyl or ($C_7$-$C_{10}$) alkylarylcarbonyl electrophilic group, with a 1,4-dihydropyridine of formula (III)

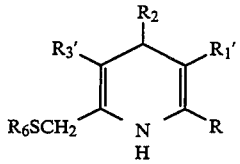

wherein R and $R_2$ are as defined above; $R_1'$ and $R_3'$ have the same meanings as $R_1$ and $R_3$ excluding the free or salified carboxyl group;

$R_6$ is hydrogen, ($C_2$-$C_6$) acyl, benzoyl or a group of formula $C(=NH)-NH_2$ or $C(=NH)-NH_2.H^+P^-$ wherein $P^-$ is the counterion of an inorganic or organic acid such as, for example, hydrochloric, hydrobromic, acetic, camphorsulphonic, mandelic, tartaric or 0,0-dibenzoyltartaric acid to give compounds of the formula Ic

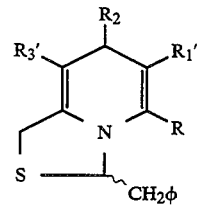

wherein R, $R_1'$, $R_2$, $R_3'$ and the symbol $\phi$ are as defined above, which may then optionally be converted into other compounds of formula I by conventional methods.

7. A pharmaceutical composition comprising a compound as recited in claim 1 together with one or more appropriate vehicles or excipients.

* * * * *